United States Patent
Kwun et al.

(10) Patent No.: US 9,176,108 B2
(45) Date of Patent: Nov. 3, 2015

(54) METHOD AND DEVICE FOR MEASURING CORROSION METAL LOSS

(75) Inventors: Hegeon Kwun, San Antonio, TX (US);
Ronald H. Peterson, Helotes, TX (US)

(73) Assignee: SOUTHWEST RESEARCH INSTITUTE, San Antonio, TX (US)

(*) Notice: Subject to any disclaimer, the term of this patent is extended or adjusted under 35 U.S.C. 154(b) by 523 days.

(21) Appl. No.: 13/558,733

(22) Filed: Jul. 26, 2012

(65) Prior Publication Data
US 2014/0028328 A1    Jan. 30, 2014

(51) Int. Cl.
| | |
|---|---|
| *G01N 27/72* | (2006.01) |
| *G01N 27/82* | (2006.01) |
| *G01N 33/38* | (2006.01) |
| *G01N 29/11* | (2006.01) |
| *G01N 29/24* | (2006.01) |
| *G01N 17/04* | (2006.01) |

(52) U.S. Cl.
CPC .............. *G01N 33/383* (2013.01); *G01N 29/11* (2013.01); *G01N 29/2412* (2013.01); *G01N 29/2437* (2013.01); *G01N 17/04* (2013.01); *G01N 2291/0258* (2013.01)

(58) Field of Classification Search
CPC .......................... G01N 27/82; G01N 27/9046
USPC .............. 324/220, 239, 240, 754.06, 754.19; 204/400, 404; 73/643
See application file for complete search history.

(56) References Cited

U.S. PATENT DOCUMENTS

| | | | |
|---|---|---|---|
| 5,456,113 A | 10/1995 | Kwun et al. | |
| 5,457,994 A | 10/1995 | Kwun et al. | |
| 5,571,037 A * | 11/1996 | Sellers | 446/188 |
| 5,581,037 A * | 12/1996 | Kwun et al. | 73/623 |
| 5,854,557 A * | 12/1998 | Tiefnig | 324/700 |
| 6,294,912 B1 | 9/2001 | Kwun | |
| 6,396,262 B2 | 5/2002 | Light et al. | |
| 6,624,628 B1 | 9/2003 | Kim et al. | |
| 6,703,600 B1 * | 3/2004 | Hodge | 250/227.11 |
| 7,722,748 B2 | 5/2010 | Chiang et al. | |
| 7,821,258 B2 | 10/2010 | Vinogradov | |
| 8,098,065 B2 | 1/2012 | Kwun et al. | |
| 2001/0017541 A1* | 8/2001 | Kwun et al. | 324/240 |
| 2002/0078752 A1* | 6/2002 | Braunling et al. | 73/627 |
| 2007/0225930 A1* | 9/2007 | Kwun et al. | 702/109 |
| 2010/0025891 A1* | 2/2010 | Droll | 264/334 |
| 2011/0259092 A1 | 10/2011 | Yu et al. | |

OTHER PUBLICATIONS

Song, et al, "Corrosion Monitoring of Reinforced Concrete Structures—A Review"; International Journal of Electrochemical Science, vol. 2 (2007) pp. 1-28.

(Continued)

*Primary Examiner* — Patrick Assouad
*Assistant Examiner* — Taqi Nasir
(74) *Attorney, Agent, or Firm* — Grossman, Tucker et al (57) ABSTRACT

A method and system for detecting corrosion metal loss. One may provide a guided wave probe that includes an electromechanical device and a corrosion probe. This may be followed by measuring a baseline guided wave attenuation value of the corrosion probe with no corrosion. One may then periodically measure the guided wave attenuation of the corrosion probe and detect an increase in guided wave attenuation values and identify metal corrosion associated with the increase in guided wave attenuation values. This may then be followed by estimating the corrosion metal loss of the metallic component.

27 Claims, 9 Drawing Sheets

(56) References Cited

OTHER PUBLICATIONS

Bartels, et al, Magnetostrictive Sensors for the Characterization of Corrosion in Rebars and Prestressing Strands, SPIE vol. 2946, pp. 40-50.
NASA; Preferred Reliability Practices; "Ultrasonic Testing of Aerospace Materials"; Practice No. PT-TE-1422,pp. 1-6; downloaded Dec. 15, 2011 from http://engineer.jpl.nasa.gov/practices/1422.pdf.
Southwest Research Institute: Technical Background on MsS; downloaded Nov. 30, 2011 from http://www.swri.org/4org/d18/nde/PDFs/msspaper.pdf.
Kwun, et al "Magnetostrictive Sensor Technology for Long-Range Guided Wave Inspection and Monitoring of Pipe", The American Society for Nondestructive Testing; The NDT Technician, vol. 10, No. 2, Apr. 2011; downloaded Dec. 31, 2011 from http://www.asnt.org/publications/tnt/tnt10-2/tnt10-2fyi.htm.

\* cited by examiner

METHOD AND DEVICE FOR MEASURING CORROSION METAL LOSS

FIELD OF THE INVENTION

The present disclosure relates generally to methods and devices for monitoring and measuring corrosion metal loss. More specifically, a device and method are disclosed that detects early metal corrosion and estimates the metal loss in selected structures, including metallic structural members that are not generally accessible.

BACKGROUND

Corrosion metal loss is one of many causes of structural damage. Various means can be used to detect and monitor corrosion in structures so that, when detected, appropriate maintenance and remedial measures may be taken to protect the structure from further corrosion damage and prolong the service life of the structure. When the metallic parts of a structure are readily accessible for testing, corrosion can be detected by using nondestructive detection methods such as visual inspection, ultrasonic thickness measurements, etc.

However, when the metallic parts of the structure are not readily accessible, such as in the case of rebar in concrete structures, suspension bridge main cables, or buried pipelines, measurements of actual corrosion damage are difficult to obtain. In these situations, corrosion damage may be inferred from indirect means that sense or measure parameters related to corrosion, such as temperature, moisture, chloride ions, strain, and/or electrochemical potential or current. Yet, these means do not provide information regarding corrosion metal loss.

To minimize corrosion related damage, detection of corrosion in its initial stages of development is needed so that corrective measures could be taken early. Accordingly, a need exists for methods that detect relatively small corrosion metal losses in the structural component, for example loss on the order of microns.

SUMMARY OF THE INVENTION

An aspect of the present disclosure relates to a method of measuring corrosion loss of a metallic component in a selected environment, comprising: (a) providing a guided wave probe that includes an electromechanical device and a corrosion probe; (b) measuring a baseline guided wave attenuation value of the corrosion probe with no corrosion; (c) periodically measuring the guided wave attenuation of the corrosion probe and detecting an increase in guided wave attenuation values and identifying metal corrosion associated with the increase in guided wave attenuation values; and (d) estimating the corrosion metal loss of the metallic component based on step (c). The corrosion probe may be formed of material similar to the metallic component to be monitored and placed proximate to such component.

The present disclosure also relates to a system for the indirect measurement of corrosion of a metallic component. Such system includes a guided wave probe that contains an electromechanical device and a corrosion probe, wherein the corrosion probe initially identifies a baseline guided wave attenuation value with no corrosion. The probe then periodically identifies guided wave attenuation at some later time. These later readings may then detect an increase in guided wave attenuation values. Such increase in guided wave attenuation provides an identification of metal corrosion. The system then estimates the corrosion metal loss of a metallic component targeted for corrosion evaluation.

BRIEF DESCRIPTION OF THE DRAWINGS

The above-mentioned and other features of this disclosure, and the manner of attaining them, may become more apparent and better understood by reference to the following description of embodiments described herein taken in conjunction with the accompanying drawings, wherein.

DETAILED DESCRIPTION

The present disclosure relates generally to methods and devices for measuring corrosion metal loss of any selected metallic component due to corrosion. The metallic components may be relatively inaccessible or difficult to access, such as piping. The components may also be structural components. For example, as structural components they may increase tensile, compressive or flexural strength of a given selected structure. "Inaccessible" may be understood herein to indicate a metallic component that is not readily accessible due to either the placement of the component relative to an observer without otherwise damaging the structure to access the component.

Accordingly, the device for measuring corrosion metal loss of a selected component herein provides a guided wave probe with a corrosion probe that is separate from the component to be evaluated. Such separate guided wave probe provides an estimate of corrosion that is representative of the metallic component under consideration. In this manner, the device herein for measuring corrosion metal loss avoids various problems associated with direct measurement of corrosion on any given structure. Such problems include the need to reliably identify early detection of corrosion so that corrective measures may be undertaken, and as noted above, where measurement of such corrosion may not be directly achieved.

The metallic component herein whose corrosion may now be reliably estimated may be at least partially or wholly set in or encased in concrete or other materials, buried underground, or otherwise affixed to a structure or tied to another structure. In some instances, removing the component may cause some degree of damage to either the component or a structure in which the component is embedded. For example, rebar located within concrete may not be accessed unless the concrete around it is removed, reducing the integrity of the concrete. Buried pipeline must be uncovered making it difficult to access the pipeline and requiring the removal of the ground above the pipeline. Portions of main cables of a suspension bridge may be difficult to access to due the location of the cable relative to the carrying surface of the bridge or due to the embedding of the main cable within portions of the bridge.

An estimate of the corrosion metal loss of a component may be obtained herein through measurements associated with guided wave probes. The guided wave probes herein may include an electromechanical device and a corrosion probe. Guided waves may be understood as mechanical or elastic stress waves in ultrasonic or sonic frequencies, 10 kHz to 500 kHz that propagate in a bounded medium that forms a portion of the probe, such as pipe, plate, rod, etc., parallel to the plane of the medium's boundary. The waves may be understood as guided because they may travel along the medium guided by the geometric boundaries of the medium. The waves may be induced by electromechanical devices such as piezoelectric transducers, electromagnetic transducers or magnetostrictive sensors. Guided wave probes may employ one or more modes of propagating the waves including longitudinal, torsional or flexural waves. Attenuation of reflected waves in the probe serves as an indicator of corrosion.

Figure 1:
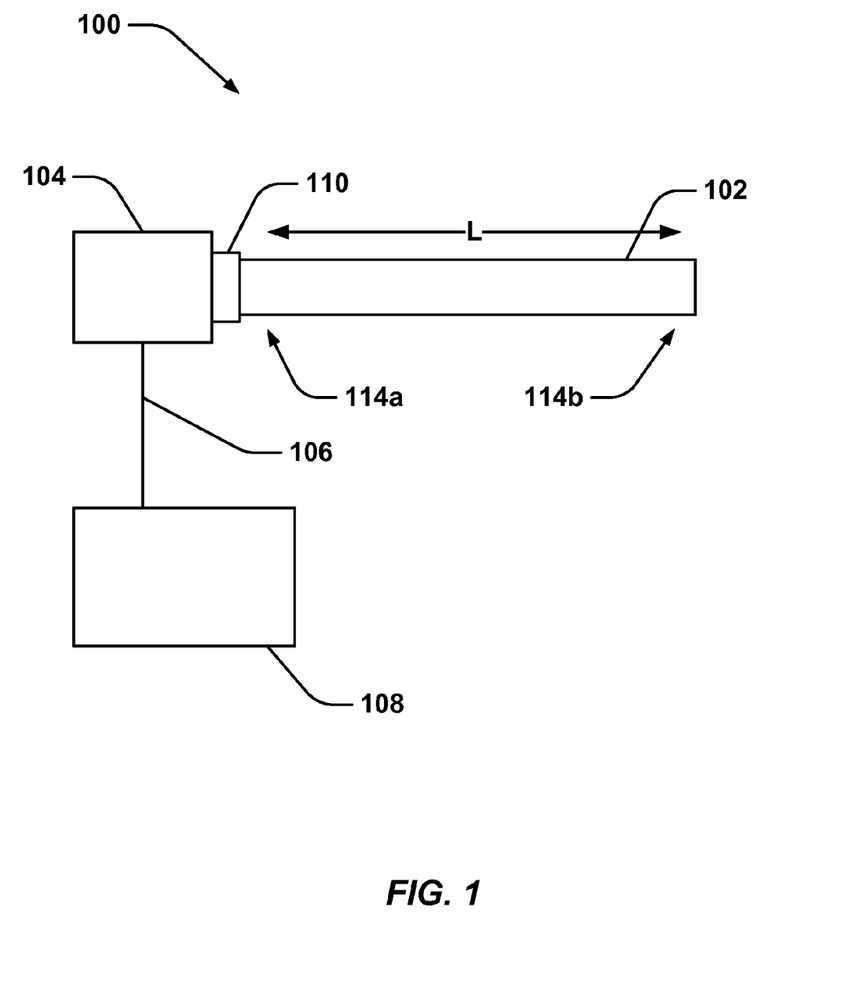
FIG. 1 illustrates an example of a guided wave probe.

Once example of a guided wave probe is illustrated in FIG. 1. The guided wave probe 100 may include a corrosion probe 102 and a transducer or sensor 104. The corrosion probe may be composed of any material that is capable of transmitting and receiving guided waves and which will provide a corrosion rate that may be relied upon to estimate the corrosion of a selected metallic component under evaluation. Accordingly, it may be appreciated that the geometry and size of the corrosion probe may vary without adversely influencing the ability of the corrosion probe to estimate corrosion, such as metal wall loss, as noted herein.

The corrosion probe may preferably have a diameter (or largest linear cross-section) in the range of 1 mm to 10 mm, including all values and ranges therein, such as 1 mm, 2 mm, 3 mm. 4 mm, 5 mm, 6 mm, 7 mm, 8 mm, 9 mm and 10 mm. The corrosion probe may have a length L in the range of 5 cm to 100 cm, including all values and ranges therein, such as 1 cm to 50 cm, 10 cm to 20 cm, etc. In addition, the corrosion probe length may be selected such that the signals reflected from the far end of the conductor may be clearly separated from each other. As alluded to above, while the corrosion probe may be formed of a cylindrical rod (i.e., having a circular cross-section), other cross-sectional shapes may be used as well such as square, rectangular, oval, etc. Furthermore, the conductor may be in the form of a plate, hollow cylinder, etc.

The guided wave probe is preferably positioned in a similar environment as the metallic component to be monitored. Reference to a similar environment is reference to the feature that the corrosion probe, in such environment, provides an indication of corrosion that is related to the corrosion that occurs on the metallic component. Accordingly, in such manner, an estimate of corrosion may be provided. Preferably, the corrosion probe may also be composed of the same or similar material of the metallic component that is being monitored for metallic corrosion loss. This technique of indirectly measuring corrosion using a separate corrosion probe may therefore provide: (1) relatively high accuracy in measuring attenuation values; (2) relatively high sensitivity in detecting early corrosion; (3) ease of calibration; (4) relatively small size and relatively low cost.

Expanding on the above, when the component of interest is formed of a specific grade of a metal or metal alloy, the corrosion probe may also be formed of the same general grade of metal or metal alloy. For example, where the component to be measured comprises rebar, the corrosion probe may comprise a metallic composition similar to the rebar, i.e. reinforcing steel bar. As alluded to above, the selection of materials that preferably exhibit similar or the same corrosion rates now assists in confirming the accuracy of the corrosion measurements.

Figure 2:
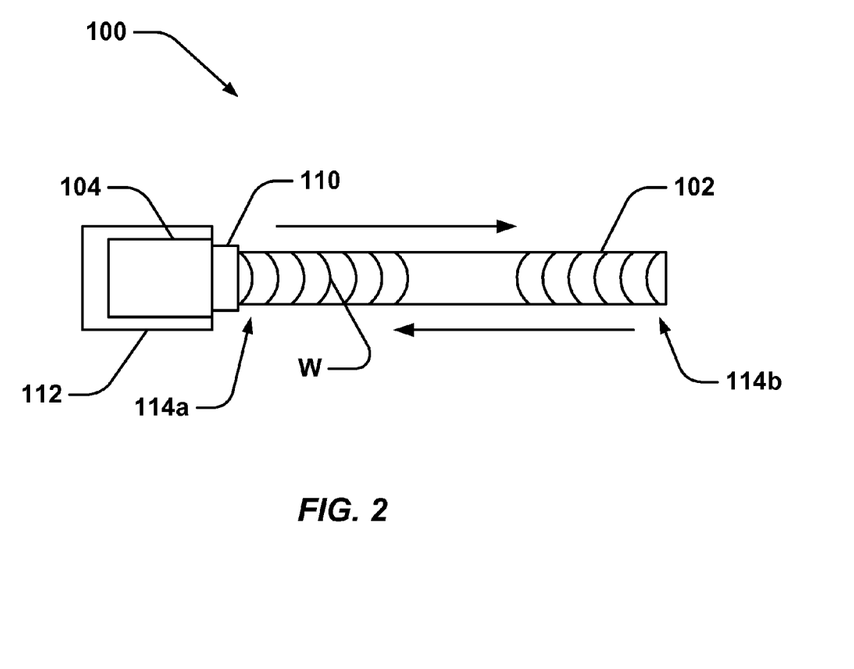
FIG. 2 illustrates an example of a guided wave probe.

The transducer or sensors for generating and/or receiving the guided waves may include piezoelectric transducers, electromagnetic acoustic transducers or magnetostrictive sensors. While FIG. 1 illustrates the transducer or sensor 104 positioned at an end 114a of the corrosion probe 102, the transducer or sensor 104 may be positioned anywhere along the corrosion probe 102. The transducer or sensors 104 may be securely coupled to the probe 102, by a coupling medium 110, such as via an adhesive or by welding. A covering 112, as illustrated in FIG. 2, may be provided over the transducer or sensor. Referring again to FIG. 1, electrical leads, or wires 106 may provide electrical communication between the probe and a detection system 108. However, wireless communication between the sensor and detection system is also contemplated. The frequencies of the waves propagated along the corrosion probe may be in the range of 10 kHz to 500 kH, including all values and ranges therein, such as 100 kHz to 300 kHz, etc.

Figure 3:
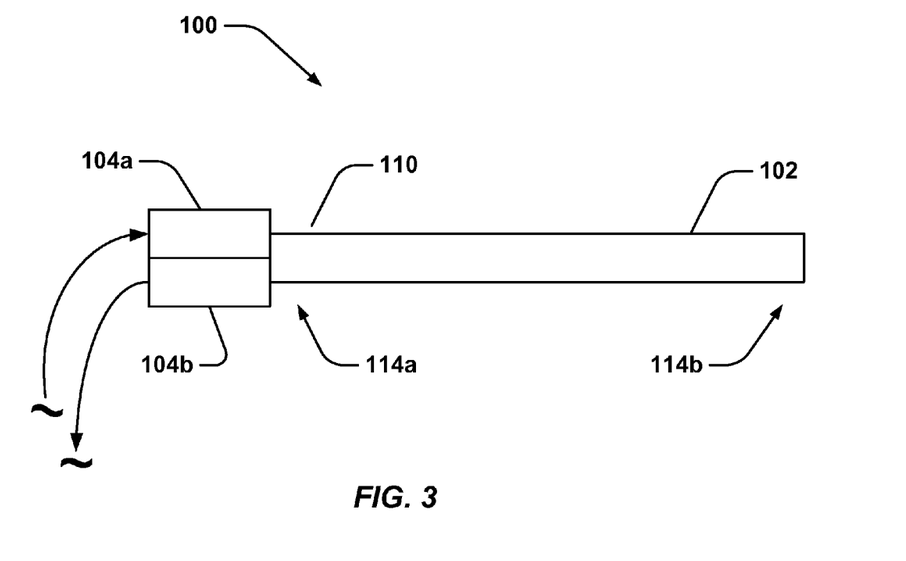
FIG. 3 illustrates an example of a guided wave probe.

While one transducer or sensor may be provided as illustrated in FIG. 1 and FIG. 2, two or more transducers or sensors 104a, 104b may be utilized as illustrated in FIG. 3. Where at least two sensors or transducers 104a, 104b are provided at least one sensor 104a may be used to generate mechanical stress waves and at least one other sensor 104b may be used to detect reflected mechanical stress waves. While the transducers or sensors 104a, 104b are illustrated as being positioned adjacent at one end 114a of the corrosion probe 102, the transducers or sensors may be positioned anywhere along the corrosion probe 102 adjacent to each other or at a distance from each other.

Referring again to FIG. 2, the induced mechanical stress waves W may propagate in the corrosion probe 102 back and forth along the length of the probe, reflecting from the probe ends 114a, 114b. The transducer or sensor 104 may detect the reflected waves and convert the waves into voltage changes, wherein the size of the voltage change may be based, for example, upon the amplitude of the waves. The voltage changes may then be transmitted to a detection system (see 108 in FIG. 1).

Figure 4:
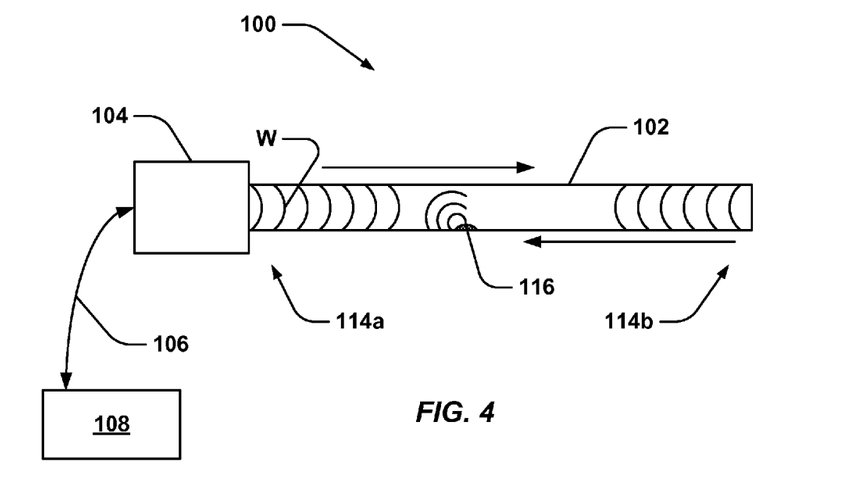
FIG. 4 illustrates an example of pulse-echo measurement techniques.

Wave attenuation may be measured employing pulse-echo or pitch-catch techniques. An example of pulse-echo techniques is illustrated in FIG. 4. As illustrated, an electrical signal communicated through the wires 106 from the detection system 108 to the probe 100 initiating the propagation of mechanical stress waves along the length of the probe. The waves are reflected by the opposite face 114b, i.e., opposing end, of the corrosion probe as well as by any discontinuities, voids or inclusions 116 due to corrosion. Corrosion oxide scale formed on the surface of metallic structures, such as rod, pipe, plate, etc., increases the guided wave attenuation, which increases with increasing degrees of corrosion. The effects of corrosion on guided wave attenuation may be greater at higher wave frequencies. The reflected guided waves are then received by the transducer or sensor and converted into an electrical signal, which is then communicated to the detection system 108.

Figure 5:
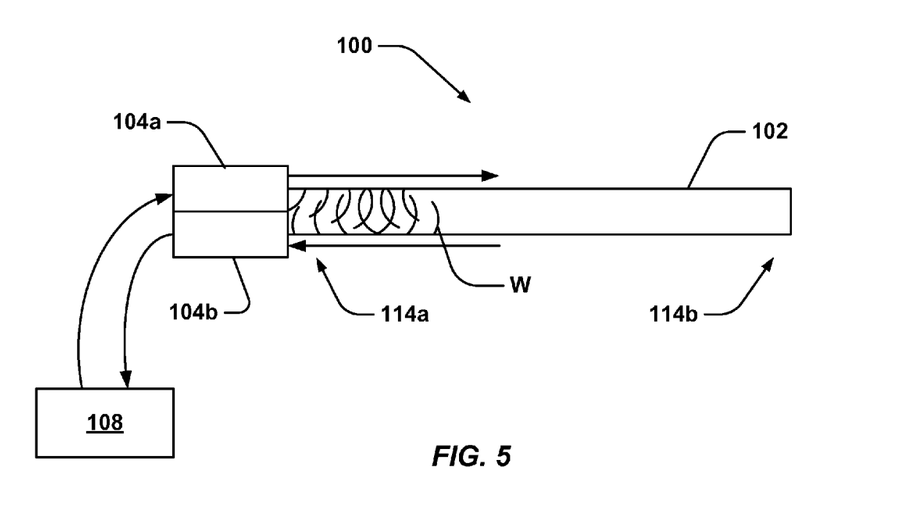
FIG. 5 illustrates an example of pitch-catch measurement techniques.

An example of pitch-catch techniques is illustrated in FIG. 5. Two or more transducers or sensors 104a, 104b may be present, wherein one transducer or sensor 104a is configured to generate mechanical stress waves and the second transducer or sensor 104b is configured to receive the reflected mechanical stress waves. Again corrosion or metal loss increases attenuation of the signal and pits, voids or discontinuities may cause additional reflections in the signal. Other techniques are plausible as well, such as through-transmission techniques.

As noted, the guided wave probe may be positioned proximate to a given structure such that the corrosion probe is subjected to a similar environment for the evaluation of corrosion of a selected metallic structure. Reference to proximate is reference to the placement of the corrosion probe at a location at or near the metallic structure so that the guided probe indicates representative corrosion data. Reference to a similar environment may be further understood herein as that situation where the corrosion probe and metallic structure for evaluation are both exposed to similar ambient temperatures (+/−10° C.), radiation (light energy) (e.g. 90% or more of the same light energy), and/or chemical environments (e.g., same pH and/or organic solvent media and/or acid-base environment). Thus, as alluded to above, rather than affixing the sensors or transducers directly to the component of interest, the corrosion probe of the guided wave probe may be used to conveniently and reliably estimate corrosion loss of any selected metallic structure.

If the metallic component to be monitored is embedded in concrete, the corrosion probe of the guided wave probe may also be embedded in the concrete and may include a concrete release agent to prevent concrete from bonding with the corrosion probe portion. In another example, if the component to be monitored is buried underground, the corrosion probe of the guided wave probe may also be buried underground. In yet a further example, if the component to be monitored forms a portion of a bridge, the guided wave probe herein may be positioned at the bridge location. As also alluded to above, the guided wave probe may be generally positioned near the component to be monitored, such as within a few millimeters or centimeters. The distance may be selected upon what is practical in a given application or what may replicate the environment of the component of interest. It may therefore be appreciated that in certain situations, one may replicate any given environment in a laboratory setting.

Using a separate probe to indirectly measure corrosion, as described herein, now permits a relatively high accuracy of measuring attenuation values that are associated with metal loss and estimating metal loss of any given metallic structural component that one may desire to monitor. As may now also be appreciated, the guided wave probe herein may be used to provide corrosion loss inspection of an at least partially or wholly inaccessible component.

Details are now provided regarding the operation of the guided wave probe. Specifically, it is noted that the baseline attenuation value and subsequent attenuation values may all be measured by generating a mechanical stress wave in the corrosion probe of the guided wave probe. The reflected mechanical stress waves may be detected by the probe and converted into voltage changes to be evaluated by the detection system and indicate the metal loss due to corrosion in the corrosion probe. Parameters that may be measured include average signal amplitude at a given location, average signal amplitude over a gated range, a root mean square value of the waveform, or combinations thereof. The corrosion metal loss of the corrosion probe based on a comparison of the subsequent attenuation value(s) to the baseline attenuation value may be calculated using corrosion models stored in memory. It may therefore be appreciated that the corrosion metal loss of the component of interest may be estimated based on the amount of corrosion of the corrosion probe.

Accordingly, to evaluate the baseline and subsequent attenuation values, the detection system may compare the voltage changes received in the baseline measurement and subsequent measurement and calculate a difference between the measurements. The difference between the subsequent measurements and the baseline measurements may then be used to determine whether the corrosion probe has corroded as the decay in the amplitude of the mechanical stress waves reflected from the ends of the corrosion probe over a given time or distance is indicative of the amount of corrosion. An estimate of the amount of corrosion exhibited by the corrosion probe in terms of metal loss may be conveniently calculated using models constructed with experimental data and stored in memory in the detection system. An estimate of corrosion exhibited by the component of interest may then be made based on the corrosion of the corrosion probe. Comparison, calculations, estimations, etc. may all be performed by one or more processors located in the system as described further below.

Figure 6:
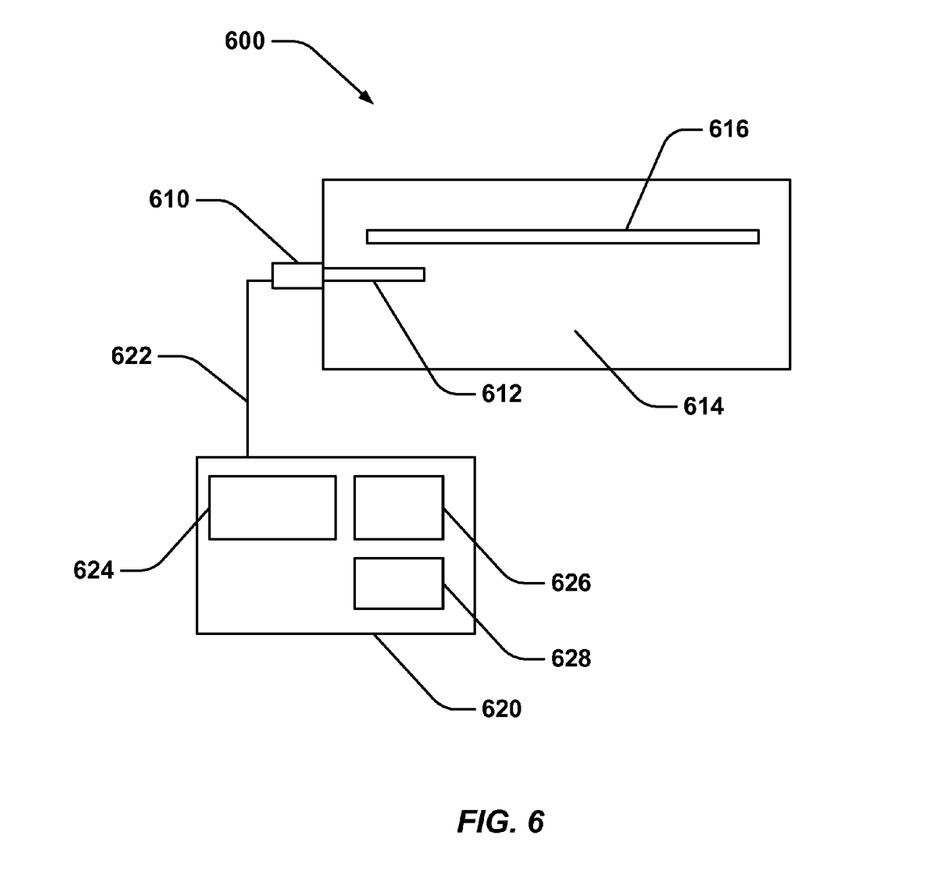
FIG. 6 illustrates a system for indirectly measuring corrosion of an at least partially inaccessible component.

A system for use in the detection of corrosion using a guided wave probe may be provided as illustrated in FIG. 6. The system 600 may include a guided wave probe 610, wherein the corrosion probe 612 of the guided wave probe 610 is positioned in an environment 614 that generally replicates the environment the component 616. As illustrated, the component 616 may be rebar and the environment 614 includes concrete. In this situation, as noted earlier, a concrete release agent may be sprayed on the corrosion probe 612.

The guided wave probe 610 is connected to the detection system 620 via one or more electrical connections or wireless connections illustrated by 622 and signals embodied by changes in voltage may be communicated over the connections 622. The detection system 620 may include on or more processors or circuitry 624 for analysis of corrosion. The detection system 620 may also include memory 626, which may be integrated into a processor or dependent from other components for the storage of data or models utilized in assessing corrosion. In addition, the detection system 620 may include one or more outputs and/or inputs 628, such as a display, keyboard, mouse, etc.

Figure 7:
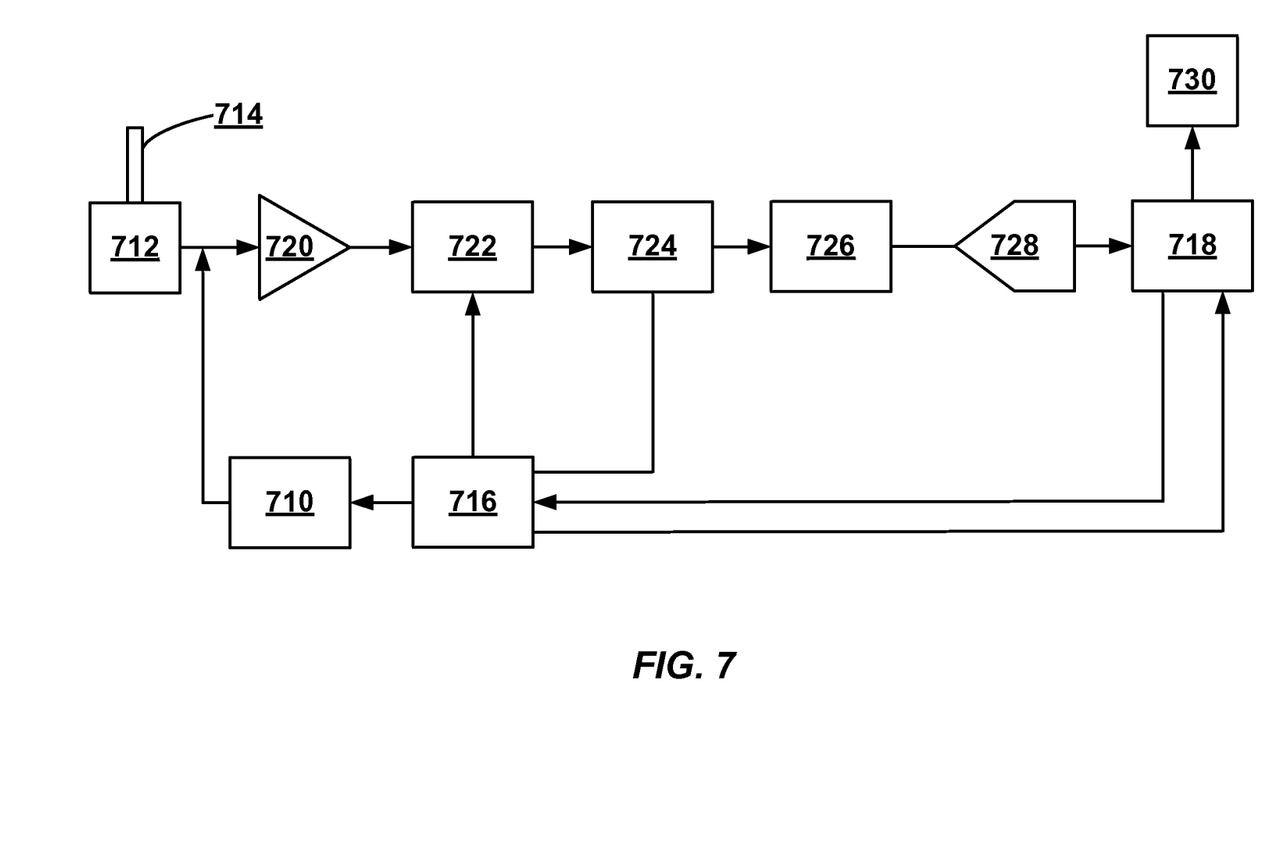
FIG. 7 illustrates an example of circuitry for use in a detection system.

The detection system may include circuitry as illustrated in FIG. 7. The circuitry 700 may apply a short current (or voltage) pulse via a pulser 710 to the guided wave probe 712 to generate the guided waves that are transmitted to the probe corrosion probe 714. This may occur at a fixed pulse repetition rate generated by the timing and control logic 716 or in a preprogrammed manner by an embedded microcontroller 718. The detected signals may then be amplified to a suitable level by a fixed-gain amplifier 720 and passed through an electronic switch 722 to reject the initial pulse and associated nonlinear saturation effects. The signal may then be input to a signal level detection circuit 724, which may measure one or more parameters indicative of signal attenuation such as the average signal amplitude at a specific location, the average signal amplitude over a gated range, or rms value of the waveform and outputs a voltage signal representing the level. The signal may then be filtered using a low pass filter 726 to eliminate electrical noise. The microcontroller 718 may then capture the signal after conversion by an analog to digital converter 728. The microcontroller may then subsequently apply a linearization algorithm to determine the corrosion wall (metal) loss calculated from a pre-established relationship and output the result digitally 730 via a display or other device.

Figure 8:
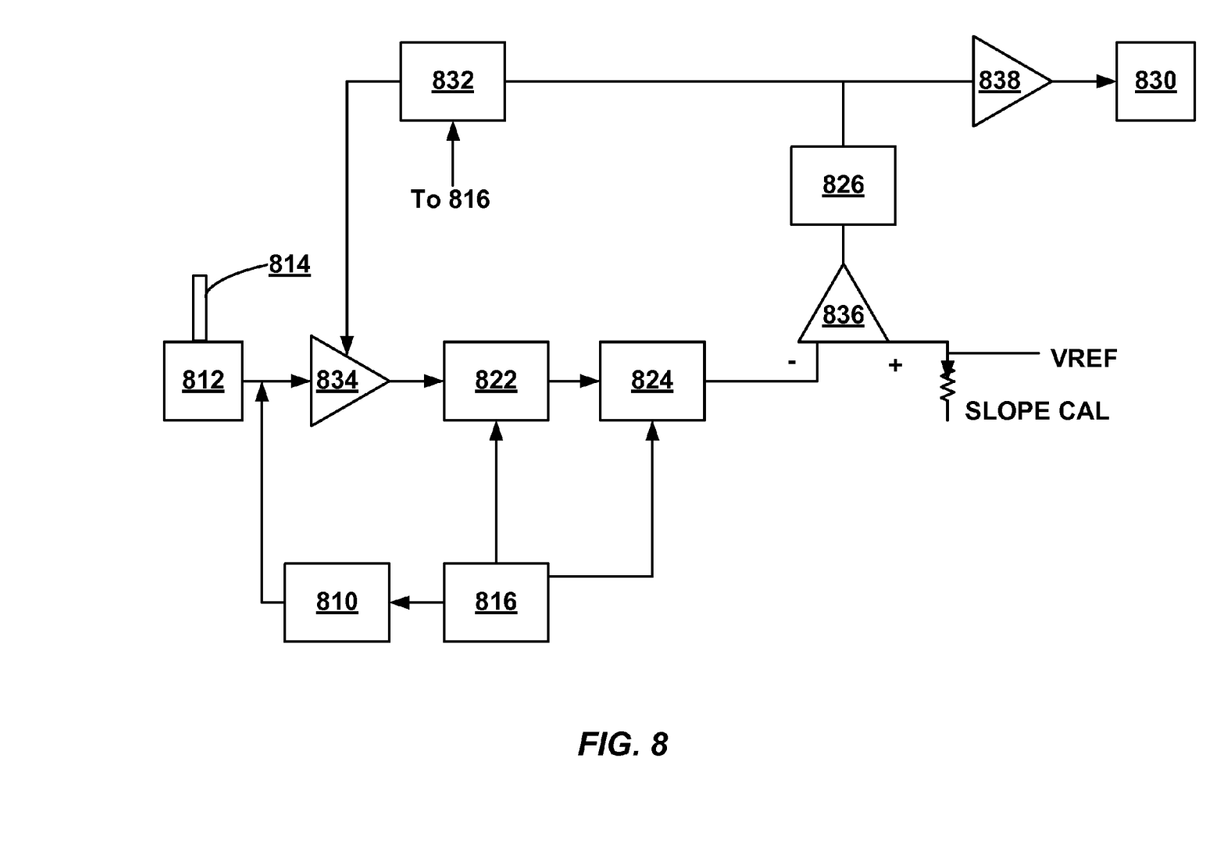
FIG. 8 illustrates an example of circuitry for use in a detection system.

The detection system may also include circuitry as illustrated in FIG. 8, wherein as between FIGS. 7 and 8, like elements carry the same last two digits, e.g., sensor 712 and sensor 812 are like elements. The circuit 800 may replace the microcontroller (718 illustrated in FIG. 7) with a closed loop feedback circuit designed to automatically adjust the linear slope of a time-gain/control circuit 832 whose output is applied to a linear-in-dB variable gain amplifier 834. The linear-in-dB function compensates for the nonlinear exponential attenuation of the guided wave signals in the conductor as a function of corrosion metal loss. The change in the DC control voltage output by the comparator 836 for the time-gain/control slope adjustment is an indicator of the change in attenuation. The data may be buffered through buffer 838 prior to output of the result digitally 830 via a display or other device.

Any of the operations described above (i.e., determining, estimating, calculating, etc.) may be implemented in a system (i.e., detection system) that includes one or more tangible storage mediums having stored thereon, individually or in combination, instructions that when executed by one or more processors perform the methods. Here, the processor may include, for example, a system CPU and/or other programmable circuitry. Also, it is intended that operations described herein may be distributed across a plurality of physical devices, such as processing structures at more than one different physical location. The storage medium may include any type of tangible medium, for example, any type of disk including floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of media suitable for storing electronic instructions. Other embodiments may be implemented as software modules executed by a programmable control device.

EXAMPLES

The following examples are presented for illustrative purposes only and therefore are not meant to limit the scope of the disclosure and claimed subject matter attached herein.

Figure 9:
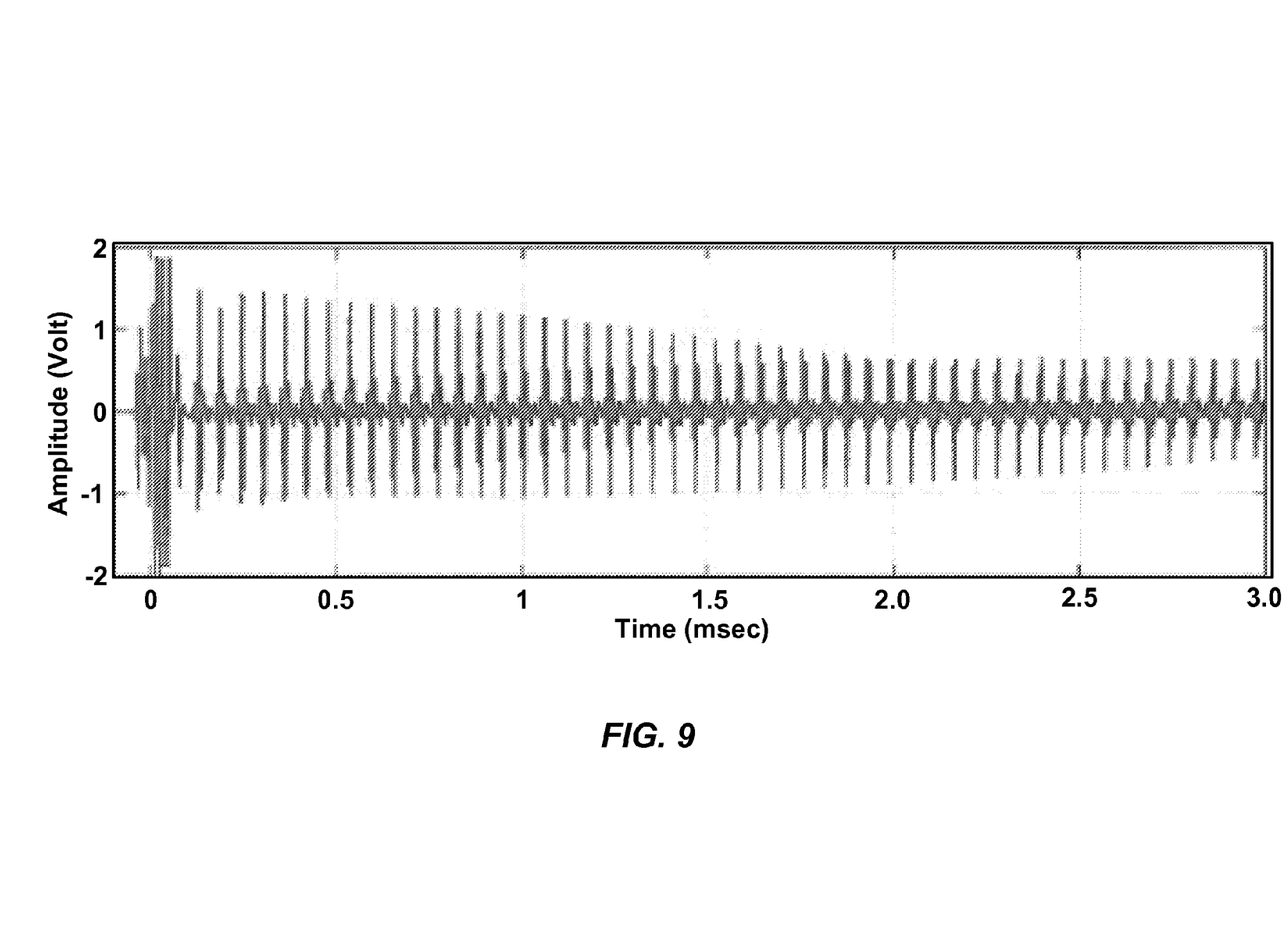
FIG. 9 illustrates an example of data obtained from a guided wave probe instrumented with a magnetostrictive sensor.

FIG. 9 illustrates an example of data obtained from a guided wave probe that was instrumented with a magnetostrictive sensor (MsS). The wave attenuation in the probe was measured by detecting multiple end reflected signals over a given time or distance, in this case 10 meters. The data was mathematically fit to an exponentially decaying curve, such as the curve expressed in Equ. 1 below:

$$A(x)=A_o\exp(-\alpha x),$$

wherein $A_o$ is a constant for curve fitting, X is the travel distance or time, and $\alpha$ is the attenuation value.

Figure 10:
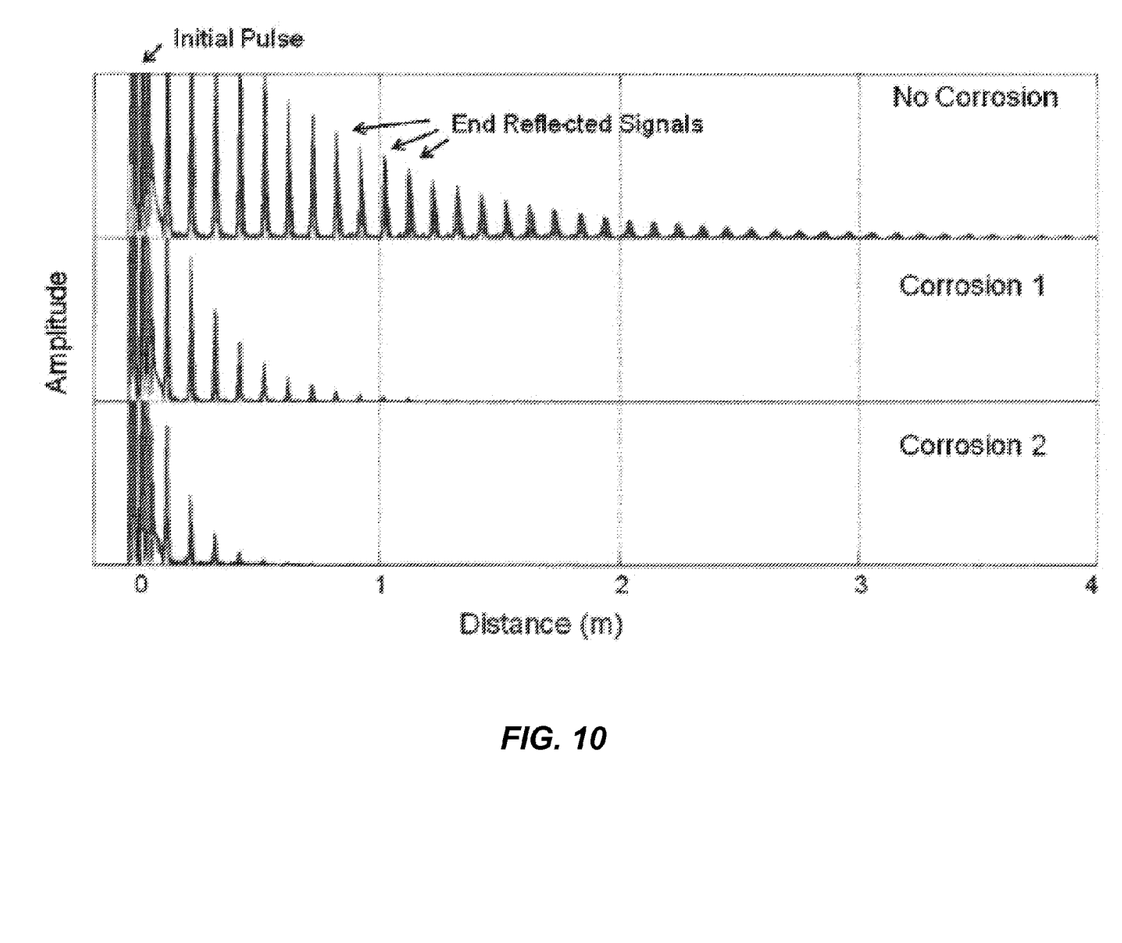
FIG. 10 illustrates an example of wave attenuation changes caused by early corrosion.

FIG. 10 illustrates an example of wave attenuation changes caused by early corrosion. In this example, the baseline attenuation in the probe was 5.8 dB/m. The attenuation increased to 18 dB/m at corrosion 1 stage and then to 34 dB/m at corrosion 2 stage. Reference to different stages is reference to different time of exposure in the subject environment. Based on the weight measurement at corrosion 2 stage, the average corrosion wall (metal) loss was determined to be 0.3 mm (or 30 microns). This example shows that the method is relatively sensitive to detect and measure early corrosion in the micron wall loss range.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

What is claimed is:

1. A method of measuring corrosion loss of a metallic component embedded in concrete, comprising:
   (a) providing a guided wave probe that includes an electromechanical device coupled to a corrosion probe, said corrosion probe being embedded in said concrete and separate from said metallic component,
   (b) measuring a baseline guided wave attenuation value of said corrosion probe with no corrosion;
   (c) periodically measuring a subsequent guided wave attenuation value of said corrosion probe and calculating an increase in guided wave attenuation value of said subsequent guided wave attenuation value in relation to said baseline guided wave attenuation value and identifying metal corrosion of said corrosion probe associated with said increase in guided wave attenuation value; and
   (d) estimating the corrosion metal loss of said embedded metallic component based on step (c).

2. The method of claim 1, wherein measuring said baseline attenuation value and measuring said subsequent attenuation value comprises generating mechanical stress waves in said corrosion probe and measuring reflected mechanical stress waves.

3. The method of claim 2, wherein said mechanical stress waves are selected from the group consisting of torsional, longitudinal, flexural and combinations thereof.

4. The method of claim 1, wherein a parameter indicative of guided wave attenuation is measured.

5. The method of claim 4, wherein said parameter is selected from the group consisting of an average signal amplitude at a given location, an average signal amplitude over a gated range, a root mean square value of the waveform, or combinations thereof.

6. The method of claim 1, wherein said attenuation is measured using a technique selected from the group consisting of pulse-echo, pitch-catch and combinations thereof.

7. The method of claim 1, wherein said corrosion probe has a length to largest cross-sectional dimension ratio of at least 2:1.

8. The method of claim 1, wherein said corrosion probe is formed of the same material as the metallic component.

9. The method of claim 1, wherein said electromechanical device includes a magnetostrictive sensor.

10. The method of claim 1, wherein said electromechanical device includes a piezoelectric transducer.

11. The method of claim 1, wherein said electromechanical device includes an electromagnetic transducer.

12. The method of claim 1 wherein said metallic component comprises a pipe.

13. The method of claim 1 wherein a concrete release agent is applied to said corrosion probe.

14. The method of claim 1 wherein said metallic component comprises a reinforcing steel member in said concrete structure.

15. A system for the indirect measurement of corrosion of a metallic component, the system comprising:
   a guided wave probe that includes an electromechanical device generating mechanical stress waves coupled to a corrosion probe embedded in concrete containing the metallic component, wherein said guided wave probe:
   (a) generates mechanical stress waves in said corrosion probe and detects reflected mechanical stress waves from said corrosion probe;

(b) provides a baseline guided wave attenuation value of said corrosion probe with no corrosion; and (c) periodically detects a subsequent guided wave attenuation value of said corrosion probe and calculates an increase in guided wave attenuation value including metal corrosion associated with said increase in guided wave attenuation; and a data recording device for storing the baseline and subsequent guided wave attenuation value; and a processor programmed to calculate the increase in the attenuation value between the baseline and the subsequent guided wave attenuation value and estimating the corrosion metal loss of said metallic component from said increase in guided wave attenuation value and metal corrosion of said corrosion probe.

16. The system of claim 15, wherein said mechanical stress waves are selected from the group consisting of torsional, longitudinal, flexural and combinations thereof.

17. The system of claim 15, wherein a parameter indicative of guided wave attenuation is measured.

18. The system of claim 17, wherein said parameter is selected from the group consisting of an average signal amplitude at a given location, an average signal amplitude over a gated range, a root mean square value of the waveform, or combinations thereof.

19. The system of claim 15, wherein said guided wave attenuation is measured using a technique selected from the group consisting of pulse-echo, pitch-catch and combinations thereof.

20. The system of claim 15, wherein said corrosion probe has a length to largest cross-sectional dimension ratio of at least 2:1.

21. The system of claim 15, wherein said corrosion probe is formed of the same material as the metallic component.

22. The system of claim 15, wherein said electromechanical device includes a magnetostrictive sensor.

23. The system of claim 15, wherein said electromechanical device includes a piezoelectric transducer.

24. The system of claim 15, wherein said electromechanical device includes an electromagnetic transducer.

25. The method of claim 15 wherein said metallic component comprises a pipe.

26. The method of claim 15 wherein said corrosion probe is embedded in said concrete and a concrete release agent is applied to said corrosion probe.

27. The method of claim 15 wherein said metallic component comprises a reinforcing steel member in said concrete structure.

\* \* \* \* \*